United States Patent [19]

Ackerman

[11] 4,437,463
[45] Mar. 20, 1984

[54] SECURING DEVICE FOR TUBE INSERTABLE IN BODY CAVITY

[75] Inventor: Bernard Ackerman, Metuchen, N.J.

[73] Assignee: Ackrad Laboratories, Inc., Garwood, N.J.

[21] Appl. No.: 321,611

[22] Filed: Nov. 16, 1981

[51] Int. Cl.³ .............................................. A61M 25/02
[52] U.S. Cl. ............................... 128/207.17; 604/179; 128/DIG. 26
[58] Field of Search ............................... 128/348–350, 128/200.26, 207.17, 207.18, DIG. 26, 327; 604/174–180

[56] References Cited

U.S. PATENT DOCUMENTS

| 3,014,482 | 12/1961 | Case | 128/291 |
| 3,080,867 | 3/1963 | Eichinger | 128/327 |
| 3,161,199 | 12/1964 | Sands | 128/348 |
| 3,880,166 | 4/1975 | Fogarty | 128/327 X |
| 3,972,321 | 8/1976 | Proctor | 128/348 |

*Primary Examiner*—Dalton L. Truluck
*Attorney, Agent, or Firm*—Lackenbach, Siegel, Marzullo, Presta & Aronson

[57] ABSTRACT

A securing device for securing endotracheal tubes to a person, and for securing similar tubes extending from body cavities, is formed of a noose in a thin-walled elastomeric tubing by means of the passage of ends of the tubing through a ring of a thick-walled tubular section. Friction between the foregoing elements and between the noose and the tube secure the device to the tube. Free ends of the tubing are passed around the body of the person to be tied or secured by means of a clamp inserted into one end of the tubing.

10 Claims, 6 Drawing Figures

SECURING DEVICE FOR TUBE INSERTABLE IN BODY CAVITY

BACKGROUND OF THE INVENTION

This invention relates to tubes, such as endotracheal tubes, which are insertable in a body cavity such as the mouth or nose.

Persons undergoing surgery or emergency-room treatment frequently require the insertion of an endotracheal or nasotracheal tube to facilitate the respiratory function as well as the administration of anaesthesia. Also, during surgery, an incision may be made through the skin and underlying tissue for the insertion of a drainage tube. The tubes are usually fabricated of a semirigid material such as polyethylene plastic; although stainless steel tubes are used for certain medical procedures and they extend or protrude from the body.

In the use of such tubes extending from the body, some sort of tie-down or holding device is utilized to secure the tube in position. Often such tubing is secured by the use of adhesive tape.

Problem arises in the use of the foregoing devices for the securing of the tubing in that such devices may not be comforting to the patient, may be overly complex to facilitate such use and, in the case of adhesives, may induce irritation and infection, as well as pain during removal and a changing of position.

SUMMARY OF THE INVENTION

The foregoing problems are overcome and other advantages are provided by a tube securing device embodying the invention which is simple in configuration, easily attached to the tube, easily removed, comfortable to wear, and free of side effects such as irritation and infection.

In accordance with the invention, the tube securing device is constructed of relatively thin walled tubing in the configuration of a lasso wherein the running noose encircles the tube. The tubing of the securing device is made of a soft elastomeric plastic and exhibits a high friction along its surface when tightly held, akin to a tacky surface, such friction forces having been observed in the thin walled tubing made of such material. Due to the friction, upon the tightening of the noose about the tube, the tube is held in a grip which prevents any slippage of the noose along the tube.

In comparing the relatively thick wall of an endotracheal tube to the relatively thin wall of the device tubing, it is noted that the thick wall has a thickness almost as great as the inner radius of the tube, being on the order of approximately 40% of the outer radius of the tube. In contrast, the thin wall of the tubing is less than approximately 15of the outer radius of the tubing. As a result, during the tightening of the noose of the tubing about the tube, the tube maintains its circular cross-sectional shape while the tubing flattens out against the wall of the tube. The flattening of the tubing directly increases the surface area and therefore the total frictional force between the tube and the tubing for a secure slip-proof grip.

In constructing the securing device, the noose is formed by passing the ends of the tubing through a ring which is conveniently formed of a section of a thick walled tube. If desired, a double noose may be formed by passing the ends of the tubing through a loop of the tubing extending through the foregoing ring. The device is secured by the tying of the ends behind the wearer's neck, or head, in the case of an endotracheal tube, or by use of a clamp secured in the end of a strand of the tubing.

The foregoing feature and further advantages of the invention are explained in the following description taken in connection with the accompanying drawings wherein:

DESCRIPTION OF THE PREFERRED EMBODIMENT

Referring now to the Figures, the securing device of the invention comprises tubing 20 of thin-walled elastomeric construction and a ring 22 formed, preferably of a section of a thick-walled tube. Both the tubing 20 and the ring 22 may be formed of a semi-rigid plastic. A hook or clamp 24 is formed of a stiff wire which may be covered with a plastic covering; a non-corrosive rod, such as a stainless hook; or even a section of single stranded, insulated electric wire being suitable for construction of the hook or clamp 24. The clamp 24 is inserted into an end of the tubing 20, the material of the tubing 20 being stretched over the wire of the clamp 24 to provide a secure bond therebetween.

Figure 1:
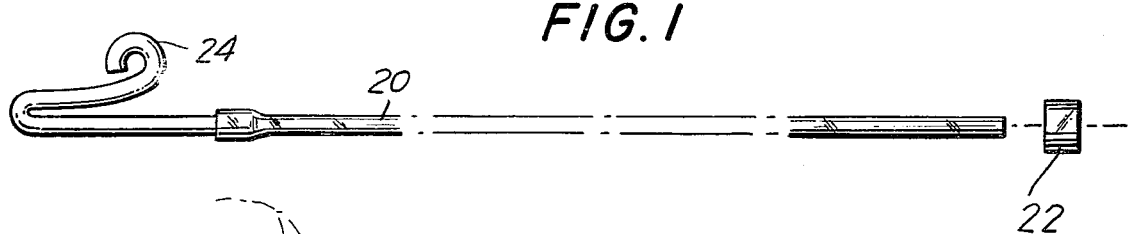
FIG. 1 is a plan view of the securing device of the invention ready for use.
Figure 2:
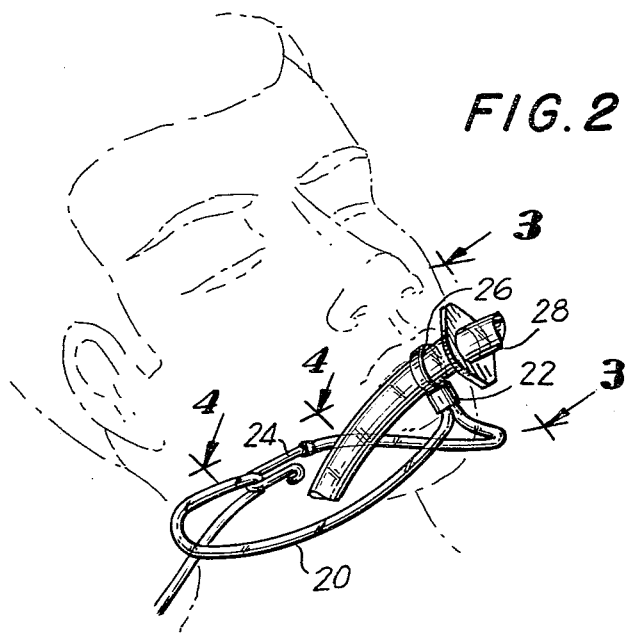
FIG. 2 is a stylized view of a person having an endotracheal tube, the Figure showing the securing of the device to the tube and to the person.
Figure 3:
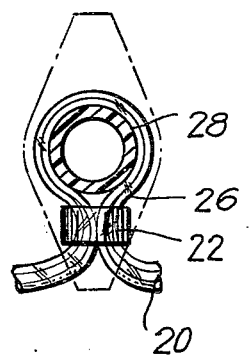
FIG. 3 shows an end view of the tube, taken along the line 3—3 in FIG. 2, with the noose of the securing device thereupon.
Figure 4:
FIG. 4 shows a passing of an end of the tubing of FIG. 1 through a clamp secured to the other end of the tubing; the view of the clamp being taken along the line 4—4 in FIG. 2.
Figure 5:
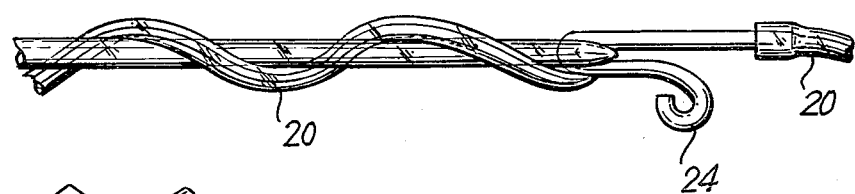
FIG. 5 shows a winding of the end about the standing part of the tubing at the clamp of FIG. 4.
Figure 6:
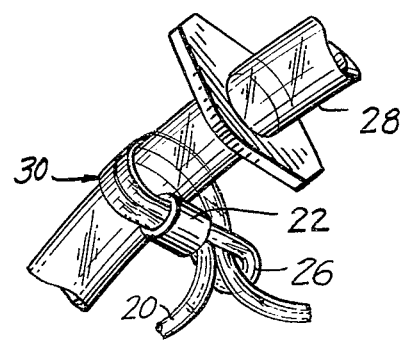
FIG. 6 is an isometric view of an end portion or the endotracheal tube with a double noose of the securing device thereon.

In use, a noose 26 is formed by passing both ends of the tubing 20 through the ring 22. The noose 26 is placed over the end of an endotracheal tube 28 extending from the person'mouth. The noose 26 is tightened about the tube 28 for a secure, non-slipping grip on the tube 28. The ends of the tubing 20 are then tied behind the neck or head of the person by securing the free end of the tubing 20 within the bight of the clamp 24. If desired, the securing device of the invention can be employed without the clamp 24, in which case both ends of the tubing 20 are free and are to be tied together as by use of a bowknot (not shown). If desired, a double noose 30 can be formed as shown in FIG. 6 by passing both ends of the tubing 20 through the single noose 26, the resulting double noose 30 being placed about the end of the tube 28. The double strands of the noose 30 provide additional gripping surfaces for a secure grip upon the tube 28. In the use of either the single or double nooses 26 or 30, along with the clamp 24, it is preferred to wind the free end of the tubing 20 about the standing part thereof as shown in FIG. 5 to insure that the securing device remains tied behind the person'neck or head.

To provide a secure grip, the tubing 20 should have the following structural features. The material used in the tubing is an elastomeric plastic such as plasticized polyvinyl chloride polyurethane or co-polymers of polyethylene such as EVA (ethylene-vinyl acetate co-polymer). The durometer of the material of the tubing 20 should be in the range of 75–85, preferably in the range of approximately 78–82. The foregoing parameters provide the desired amount of frictional force between the tubing 20 and the tube 28 to permit facile tightening of the device for use on tubes of plastic, metal and glass. In order to insure that the tubing 20 flattens out around the tube 28, the wall of the tubing 20 should be less than 15% of the tubing's outside diameter. In an experimental model of the invention, tubing 20 has an inner diameter of 0.106–0.112 inches and a wall thickness of 0.016 inch.

It should also be appreciated that the securing device of the invention would be attached to a tube, such as the tube 28, whether the tube be an endotracheal tube, extending from the mouth of a patient, a nastracheal tube, extending from the nose of a patient, or a drain tube extending from a surgical incision of the patient. In each case, the free ends of the tubing 20 are to be passed around the body of the wearer, and secured by tying or by use of the clamp 24. Alternatively, the free ends of the tubing 20 may even be connected by other well known tying means, such as "Velco" straps which are compatible interlocking hook and loop elements manufactured by the Velcro Corporation of America, New York, New York.

It is to be understood that the above-described embodiments of the invention are illustrative only and that modification thereof may occur to those skilled in the art. Accordingly, this invention is not to be regarded as being limited to the embodiments disclosed herein, but is to be limited only as defined by the appended claims.

What is claimed is:

1. A device for securing a tube extending from a body, said device comprising:
    a thin-walled tubing of elastomeric material;
    a ring formed of a rigid tubular section;
    a noose formed by the passage of said tubing through said ring, said noose being adapted for encircling said tube without occluding same; said tubing being of such a size that when pulled to a snug fit flattens out against the wall of said tube, thereby increasing the surface contact area and thus the total frictional force between said tube and said tubing resulting in a secure slip-proof grip of said noose about said tube extending from said body;
    the ends of said tubing being flexibly extendable about a portion of said body for engagement with each other by means secured to at least one end of said tubing so as to secure said tube to said body; and
    said ring being made of an elastomeric material having a durometer in the range of 75–85.

2. A device according to claims 1, wherein a loop of the noose comprises a plurality of strands of tubing.

3. A device according to claim 2, wherein said noose is a double noose.

4. A device according to claim 1, wherein said elastomeric material is a plastic selected from the group comprising a plasticized polyvinyl chloride polyurethane, co-polymers of polyethylene and other like elastomeric materials.

5. A device according to claim 1, wherein said thin-walled tubing comprises a tubular material having a wall thickness no greater than 15% of the outside diameter of said tubular material.

6. A device for securing a tube extending from a body, said device comprising:
    a thin-walled tubing of elastomeric material;
    a ring formed of a rigid tubular section;
    a noose formed by the passage of said tubing through said ring, said noose being adapted for encircling said tube without occluding same; said tubing being of such a size that when pulled to a snug fit flattens out against the wall of said tube, thereby increasing the surface contact area and thus the total frictional force between said tube and said tubing resulting in a secure slip-proof grip of said noose about said tube extending from said body;
    the ends of said tubing being flexibly extendable about a portion of said body for engagement with each other by means secured to at least one end of said tubing so as to secure said tube to said body; and
    said thin-walled tubing comprising a tubular material having a wall thickness no greater than 15% of the outside diameter of said tubular material.

7. A device according to claim 6, wherein a loop of the noose comprises a plurality of strands of tubing.

8. A device according to claim 7, wherein said noose is a double noose.

9. A device according to claim 6, wherein said ring is made of an elastomeric material having a durometer in the range of 75–85.

10. A device for securing a tube extending from a body, said device comprising:
    a thin-walled tubing of elastomeric material;
    a ring formed of a rigid tubular section;
    a noose formed by the passage of said tubing through said ring, said noose being adapted for encircling said tube without occluding same; said tubing being of such a size that when pulled to a snug fit flattens out against the wall of said tube, thereby increasing the surface contact area and thus the total frictional force between said tube and said tubing resulting in a secure slip-proof grip of said noose about said tube extending from said body;
    the ends of said tubing being flexibly extendable about a portion of said body for engagement with each other by means of interlocking hook and loop elements provided on the ends of said tubing so as to secure said tube to said body.

* * * * *